United States Patent [19]

Letchworth et al.

[11] 4,001,405
[45] Jan. 4, 1977

[54] PHOSPHONATE SYNERGISTS

[75] Inventors: Peter E. Letchworth, Cupertino, Calif.; Edward D. Weil, Hastings-on-Hudson, N.Y.

[73] Assignee: Stauffer Chemical Company, Westport, Conn.

[22] Filed: Mar. 26, 1975

[21] Appl. No.: 562,368

Related U.S. Application Data

[63] Continuation-in-part of Ser. No. 427,160, Dec. 21, 1973, abandoned, which is a continuation of Ser. No. 158,542, June 30, 1971, abandoned.

[52] U.S. Cl. .............................. 424/210; 424/219
[51] Int. Cl.$^2$ ........................................ A01N 9/36
[58] Field of Search ........................... 424/210, 219

[56] References Cited

UNITED STATES PATENTS 3,301,749   1/1967   Sakai et al. ..................... 424/210

OTHER PUBLICATIONS

Montgomery et al., Def. Pub. No. T875,002 (pub. June 2, 1970).

*Primary Examiner*—V. D. Turner
*Attorney, Agent, or Firm*—Daniel C. Block

[57] ABSTRACT

This invention relates to insecticidal active compositions. More specifically, this invention relates to the use of O,O'-dipropargyl chloromethylphosphonate as a synergist for a commercially available insecticidal active compound defined as O,O-dimethyl-O-(2-methoxy-4-cyanophenyl)-phosphorothioate.

2 Claims, No Drawings

PHOSPHONATE SYNERGISTS

CROSS-REFERENCE TO RELATED APPLICATION

This application is a continuation-in-part of application Ser. No. 427,160 filed Dec. 21, 1973 which is a continuation of application Ser. No. 158,542 filed June 30, 1971, now both abandoned.

DESCRIPTION OF THE INVENTION

There are several insecticidal active compounds commercially available. Some of these compounds are all-purpose insecticides, while others have special-purpose structures. Some of these insecticides are as follows: pyrethrum; methoxychlor, defined as 2,2-bis-(p-methoxyphenyl)-1,1,1-trichloroethane; 1-naphthyl N-methylcarbamate, sold under the tradename "SEVIN"; O,O-dimethyl-O-(2-methoxy-4-cyanophenyl)-phosphorothioate; and N-(mercaptomethyl)phthalimide S-(O,O-dimethylphosphorodithioate), sold under the tradename "IMIDAN".

These insecticides are immediately toxic to a large number of insect pests at different concentrations varying with the resistance of the insects sought to be controlled. The endeavor to extend the usefulness of these insecticides by increasing their effectiveness and lowering their cost has led to extensive studies in another class of insecticidal material, customarily referred to as synergists. Among the many synergists employed, the alkyl oxides, specifically piperonyl butoxide, have been widely used. While these compositions enhance the usefulness of the insecticides, they do not measure up to the low cost that is desirable along with increased effectiveness.

The synergist compound of the present invention is known and the manner in which it is manufactured is also known. However, its use as a synergist has not been disclosed or published. In the use of the synergist compound, O,O'-dipropargyl chloromethylphosphonate, of the present invention it is merely admixed with the insecticidal active compound. The amount of synergist admixed with the insecticidal active compound can range from about 1 to 0.1 to about 1 to 10 parts insecticidal active compound to synergist compound. After the insecticidal active compound and the synergist are mixed together, they are applied to the habitat of the insect to be controlled in a conventional manner as indicated for the recommended use of the insecticidal active compound. That is to say, the synergist that is added to the insecticidal active composition does not alter the manner in which the insecticidal active compound is customarily used. Thus, the manner in which the insecticidal active compounds are used will be dictated by the manner in which the insecticidal active compound is recommended by the manufacturer.

In order to illustrate the merits of the present invention, the following insecticidal evaluation test was conducted.

I. House fly [*Musca domestica* (L.)]

A. Film residue

A stock solution containing 100 μg/ml of the toxicant in an appropriate solvent is prepared. Aliquots of this solution are combined with one ml. of an acetone-peanut oil solution in a dish, 55 mm. in diameter, and allowed to dry. The aliquots are varied to achieve desired toxicant concentrations ranging from 100 μg per dish to that at which 50% mortality is obtained. The dishes are placed in a circular cardboard cage, closed on the bottom with cellophane and covered on top with cloth netting. Twenty-five female houseflies are introduced into the cage and the percent mortality is recorded after 48 hours. LD-50 values are expressed in terms of μg 25 male flies in Table I.

TABLE I

| Compound | Average $LD_{50}$ Values μg/25 Female Houseflies |
|---|---|
| O,O-dimethyl-O-(2-methoxy-4-cyanophenyl)-phosphorothioate | 5.0 |
| O,O'-dipropargyl chloromethyl-phosphonate (synergist) | >100.0 |
| O,O-dimethyl-O-(2-methoxy-4-cyanophenyl)-phosphorothioate + synergist 1:0.10 ratio | 3.3 |
| O,O-dimethyl-O-(2-methoxy-4-cyanophenyl)-phosphorothioate + synergist 1:0.25 ratio | 2.9 |
| O,O-dimethyl-O-(2-methoxy-4-cyanophenyl)-phosphorothioate + synergist 1:0.50 ratio | 2.4 |
| O,O-dimethyl-O-(2-methoxy-4-cyanophenyl)-phosphorothioate + synergist 1:1.00 ratio | 1.9 |
| O,O-dimethyl-O-(2-methoxy-4-cyanophenyl)-phosphorothioate + synergist 1:2.50 ratio | 2.1 |
| O,O-dimethyl-O-(2-methoxy-4-cyanophenyl)-phosphorothioate + synergist 1:5.00 ratio | 2.0 |
| O,O-dimethyl-O-(2-methoxy-4-cyanophenyl)-phosphorothioate + synergist 1:10.00 ratio | 2.0 |

II. German Cockroach [*Blattella germanica* (Linne)]

Aliquots of an acetone solution of the toxicant plus synergist are applied to the abdomen of ten 1-month-old cockroaches by means of a syringe and needle. Concentrations of the toxicant range from 20 μg/cockroach to that at which 50% mortality is obtained. Treated roaches are then confined to a circular cardboard cage sealed on one end with cellophane and covered by cloth netting on the other. Percent mortality is recorded after 72 hours, and LD-50 values are expressed as micrograms of toxicant per roach in Table II.

TABLE II

| Compound | Average $LD_{50}$ Values μg/roach |
|---|---|
| O,O-dimethyl-O-(2-methoxy-4-cyanophenyl)-phosphorothioate | 10 |
| O,O'-dipropargyl chloromethyl-phosphonate (synergist) | >20 |
| O,O-dimethyl-O-(2-methoxy-4-cyanophenyl)-phosphorothioate + synergist 1:0.10 ratio | 5.00 |
| O,O-dimethyl-O-(2-methoxy-4-cyanophenyl)-phosphorothioate + synergist 1:0.50 ratio | 1.00 |
| O,O-dimethyl-O-(2-methoxy-4-cyanophenyl)-phosphorothioate + synergist 1:1.00 ratio | 0.90 |
| O,O-dimethyl-O-(2-methoxy-4-cyanophenyl)-phosphorothioate + synergist 1:5.00 ratio | 0.30 |
| O,O-dimethyl-O-(2-methoxy-4-cyanophenyl)-phosphorothioate + synergist | |

TABLE II-continued

| | |
|---|---|
| 1:10.00 ratio | 0.30 |

What is claimed is:

1. An insecticidal composition comprising an insecticidally effective amount of an insecticidal compound consisting of O,O-dimethyl-O-(2-methoxy-4-cyanophenyl)-phosphorothioate and a synergistic amount of a synergist compound consisting of O,O'-dipropargyl chloromethylphosphonate; said compounds being present in an amount of about 1 part insecticidal compound to about 0.1 to 10 parts synergist compound.

2. A method of controlling insects wherein an insecticidally effective amount of an insecticidal compound consisting of O,O-dimethyl-0-(2-methoxy-4-cyanophenyl)-phosphorothioate is admixed with a synergistic effective amount of a synergist compound consisting of O,O'-dipropargyl chloromethylphosphonate and contacted with the habitat of the insect to be controlled; said compounds being present in an amount of about 1 part insecticidal compound to about 0.1 to 10 parts synergist compound.

* * * * *